United States Patent [19]

Malras et al.

[11] Patent Number: 5,116,825
[45] Date of Patent: May 26, 1992

[54] PHYTOSANITARY COMPOSITION, ITS PROCESS FOR PREPARATION AND ITS USE FOR TREATING CRYPTOGAMIC DISEASES

[75] Inventors: Jean-Claude Malras, Erquinghem-sur-la-Lys; Serge Gosset, Lestrem, both of France

[73] Assignee: Roquette Freres, Lestrem, France

[21] Appl. No.: 500,046

[22] Filed: Mar. 27, 1990

[30] Foreign Application Priority Data

May 29, 1989 [FR] France ................... 89 07003

[51] Int. Cl.$^5$ ............... A01N 43/16; A01N 63/02; A01N 65/00; A01N 47/38
[52] U.S. Cl. ................... 514/58; 514/468; 514/231.2; 514/63; 514/54; 536/103
[58] Field of Search ............ 514/58, 231.2, 468, 514/63; 560/256; 536/103; 424/488

[56] References Cited

U.S. PATENT DOCUMENTS

| | | | |
|---|---|---|---|
| 4,226,983 | 10/1980 | Lane | 536/103 |
| 4,303,787 | 12/1981 | Horikoshi et al. | 536/103 |
| 4,596,795 | 6/1986 | Pitha | 514/58 |
| 4,769,242 | 9/1988 | Shibanai | 514/58 |
| 4,834,985 | 5/1989 | Elger et al. | 424/488 |
| 4,923,853 | 5/1990 | Szejtli et al. | 514/58 |
| 4,954,495 | 9/1990 | Strumpf et al. | 514/231.2 |
| 4,983,587 | 1/1991 | Speakman et al. | 514/468 |

FOREIGN PATENT DOCUMENTS

| | | | |
|---|---|---|---|
| 4012312 | 6/1965 | Japan | 514/58 |
| 60-72804 | 4/1985 | Japan | 514/58 |
| 8603939 | 7/1986 | PCT Int'l Appl. | 514/58 |
| 0898001 | 6/1962 | United Kingdom | 514/58 |

OTHER PUBLICATIONS

Central Patents Index, Basic Abstracts Journal, section c, week 83-38, Nov. 16, 1983 Derwent Publishers Ltd, London, GB * N°83-767169/38 * & JP-A-58 134 004 (Kyushu Sankyo) Aug. 10, 1983.

Chemical Patents Index, Basic Abstracts Journal, section c, week 88/20, Jul. 13, 1988, Derwent Publications Ltd, London, GB * N° 88-137240/20 * & JP-A-63 079 802 (Nihon Noyaku) Apr. 9, 1988.

*Primary Examiner*—Ronald W. Griffin
*Assistant Examiner*—Louise Leary
*Attorney, Agent, or Firm*—Larson and Taylor

[57] ABSTRACT

Phytosanitary composition, useful particularly for the protection of plants against crypotogamic diseases, characterized in that it contains a source of $Cu^{++}$ copper ions and at least one cyclodextrin adapted to form complexes with said copper ions.

27 Claims, No Drawings

PHYTOSANITARY COMPOSITION, ITS PROCESS FOR PREPARATION AND ITS USE FOR TREATING CRYPTOGAMIC DISEASES

The present invention relates, as novel industrial products, to phytosanitary compositions based on copper and cyclodextrins, useful particularly in the protection of plants against cryptogamic diseases, as well as their process of preparation.

By cryptogamic diseases, is meant any infection which can be caused by cryptogames and particulary by so-called "cellular" cryptogames, such as fungi, algi, cyanophytes or bacteria or by so-called "vascular" cryptogames such as ferns, of the Equisetineae or Lycopodineae classes.

The invention is directed particularly at the preparation and use of these novel compositions for the protection of cultivated plants against diseases due to fungi of the peronosporales' order.

It is aimed finally very particularly and the preparation and the use of said novel compositions for the protection of vines against *Plasmopara viticola*, also called "downy mildew" of the grapevine.

It is known that, among phytopathogenic agents, cryptogames and in particular mushrooms or "fungi" can attack and then infest all or a part of many plants, following which, if sanitary protective measures are insufficient, unsuitable or too late, said phytopathogenic fungi can cause real epidemics preventing any use or valorization, particularly as foodstuffs, of these crops.

Among the fungal diseases which can cause serious epidemics to cultivated plants, mention must be made of diseases caused by mushrooms of the Peronosporales' order, especially those commonly called "mildews" and belonging to the Plasmopara, Perenospora, Trachysphaera or Bremia genera.

It is possible to cite in particular the downy mildew of the vine (*Plasmopara viticola*), potatoe mildew or tomato mildew (*Phytophtora infestans*), tobacco mildew (*Peronospora tabacina*) and banana mildew (*Tachysphaera fructigena*).

The means employed for protecting plants against this type of cryptogamic disease can be classed in two large categories, according to the nature of their constituent:
cupric compositions, that is to say containing a source of $Cu^{++}$ copper ions, the latter being the active material, particularly fungicide and/or bactericide,
"acupric" synthetic organic products whose activity, particularly fungicidal and/or bactericidal, is not associated specifically with the presence of a source of $Cu^{++}$ copper ions, but with that of organic molecules derived, for example, from carbamic acid, phtalimide or quinoline.

It should be noted that these active organic molecules can be proposed in the form of metallic salts, including the form of copper salts. However, in this case, the nature of the metal present is not preponderant in terms of anticryptogamic activity. In fact, the activity of the entity organic molecule/metal remains fundamentally connected with the nature of the organic molecule employed and the metal, especially due to its none or to its weak availability in ionic form, does not play any part here or only a negligible part.

As regards the role of copper $Cu^{++}$ ions as active substance useful as means of protection of plants against cryptogamic diseases, especially those caused by mushrooms belonging to the Peronosporales' order, reference may be made to the preventive and/or curative treatment of the vine mildew (*Plasmopara viticola*), infection whose biology and epidemiology have been widely studied since 1878, at which date this mushroom originating in America made its appearance in European vineyards.

The development cycle of *Plasmopara viticola*, disclosed, for example, in patent FR 2,385,329, comprises the stages which will be recalled below.

Oospores formed in the Autumn "hibernate" until the Spring on the dead leaves and other organic materials of the vine which have fallen to the ground. At this time, they encounter conditions favourable for their development, the latter being manifested by the formation of macroconidiae which, carried by the wind or other vector agents, arrive on various parts of the plant in a renewed vegetative phase, particularly the foliage.

If the conditions, particularly climatic (humidity, temperature) are favourable, the "zoospores" stage is reached through which the macroconidiae give birth to small mobile spores or zoospores which swim by means of their flagellae and fix themselves close to the stomata of the leave. They germinate at this level by emitting a filament which penetrates and develops in mycelium form in the foliose tissues which are thus altered.

There result therefrom regular spots of olive green or greenish yellow with a shiny glint at the level of which the tissues acquire a certain transparency. This is the "grease-spot" stage, a visible symptom of the infection.

Some days later there appears on the lower surface of the leaves a fine white film constituted by "conidiophore filaments" bearing small clusters of conidiae. Creating a secondary infection, the latter are dispersed over the infectable members of the vine and under favourable conditions of temperature and humidity, germinate in their turn by generating further zoospores.

The infection is thus propagated until the Autumn, at which time said oospores are formed which hibernate until the following Spring.

As has been stated, this propagation occurs particularly at the level of the leaves but it can also attack in the same manner diseased members, young shoots and grapes. The mildew of the vine, if it is not combated in due time and with adequate means, may be seriously detrimental to the grape production. Severe attacks of the foliage cause complete dessication and fall of foliage; a consequence is a weakening of the vine-stock; the grapes, poorly nourished, no longer grow bigger, remain sour and give a poor quality vine. In addition, as has been stated, the mildew can attack and alter the grapes directly and this, at very different stages of fructification.

The role of the copper $Cu^{++}$ ions as active substance useful as means of protection of plants against diseases caused by fungi belonging to the Peronosporales' order, in particular as a means of preventive and/or curative treatment of mildew of the vine, has long been known.

It is known for example that copper sulphate permits *Plasmopara viticola* to be effectively combated but that, due to the fact of its acidity and its richness in soluble copper, it shows a certain degree of phytotoxicity and causes among other things, an alteration of leave tissues in the form of burns.

This product has been abandoned in favour of a neutralized form, and this neutralization can be done advantageously with calcium hydroxide or sodium carbonate.

The mixture copper sulphate/calcium hydroxide employed in known compositions under the successive names of "medocaine medium" then "bordelaise medium" or "Bordeaux mixture" has encountered a very great success during the first half of this century due to the fact that it has overall enabled the viticulture industry to overcome the problems which appeared with the introduction of rootstocks of American origin responsible for the proliferation of grapevine mildew.

Another frequently used composition, known by the name of "Burgundian mixture" is constituted from a copper sulphate/sodium carbonate mixture.

On the other hand, copper salts other than the sulphate have been used with success in this type of preparation, in particular copper oxychloride, copper hydroxide and cuprous oxide.

These preparations are generally in the form of wettable powders intended to be sprayed on the plants to be protected or portions of the latter, particularly leaves.

They are generally used in the proportion of 300 to 500 g of metallic copper $Cu^{++}$ per hectoliter of mixture, namely 3 to 5 kg of metallic copper $Cu^{++}$ per hectar knowing that the volume of mixture employed to treat a hectar is conventionally 1000 liters.

These cupric specialities generally act as so-called "contact" phytosanitary agents. This is the case moreover with certain "acupric" synthetic organic substances such as the derivatives of carbamic acid known, for example, under the names "zinebe", "manebe" or "mancozebe" or derivatives of phthalimide known, for example, under the names "captafol" or "folpet".

These phytosanitary contact agents are differenciated from so-called "systemic" synthetic substances such as the alkylphosphites for which the active substance is carried by the sap, from the point of application (leaves) to the other parts of the plant.

It should be recalled that, in the biology and epidemiology of grapevine mildew, the determining and recurrent factor for the development of *Plasmopara viticola* is the presence of high humidity (abondant rain and/or dew) enabling the formation, at least for some hours, of a film or of droplets of water on the green parts of plant, the leaves especially, and, by the same circumstance, ensuring the germination of the conidiae and the dissemination of the infection in the form of mobile zoospores.

From an other aspect, it has been long known that the environmental humidity and that of the treated leaves have a predominant importance in the effectiveness of the phytosanitary treatment applied, especially in the case of a treatment employing a cupric composition.

Thus, after spraying, droplets of a conventional cupric composition, of the "Bordeaux mixture" type, for example, leave by being dried on the vine, the deposit formed by insoluble cupric compounds. It is generally accepted that, due to the effect of rain and of waterings charged with carbon dioxide gas, the insoluble deposit forms little by little a soluble cupric compound: copper hydroxide. This compound releases in its turn soluble copper in the form of copper ions $Cu^{++}$. It is in this form that the copper diffuses into the water drops on the surface of the vine and that it acts as active substance poisoning the zoospores of the mildew.

It has been demonstrated on several occasions that a very small amount of free soluble copper, hardly of the order of some ppm (parts per million), was enough to ensure this antifungal action against *Plasmopara viticola*.

The principal defect of the cupric phytosanitary compositions, that is to say using the action of copper ions $Cu^{++}$ as active substance, resides in the amount of copper salts to be employed to obtain a sufficient effectiveness of treatment.

In fact, only a minimum portion of the copper ion source $Cu^{++}$ applied actually acts as fungicidal agent, the remaining part being washed by the rain and this, even in the case of "Bordeaux mixture" for which the addition of lime has the effect of simultaneously neutralizing the copper sulphate and procuring better adherence of the mixture to the plant.

A part from the excessive cost due to insufficient yield of these cupric specialities, their repeated use is liable to result in an accumulation of copper salts in the soil which is particularly damaging to the environment and/or of exacerbating their potential phytotoxicity by causing depressing effects on the growth of the plant.

Many attemps have been made in order to improve the persistance over the time of copper ion $Cu^{++}$ in amount and distribution sufficient to ensure effective reaction against the appearance and/or the development of mildew of the vine.

The already mentioned French patent 2,385,329 recommends the fixing of the cupric ions to a micronized resin capable of exchanging said cupric ions with the cations present in the moisture covering the uncovered organs of the plant. It is stated that such exchanges can significantly improve the persistance over time of the antifungal activity of the $Cu^{++}$ ions and this, especially when they are associated with a bentonite clay also micronized capable of swelling and of forming a gel in contact with water.

The preparation of the antioryptogamic compositions as claimed appears however complex and delicate. The bentonite used must particularly possess certain very specific characteristics which have to enable, among other things, to avoid the internal reactions tending to form insoluble salts with the copper ions and to confer on the cuprobentonitic gel a weakly acid reaction, the optimum pH being situated at about 6.5. Questions can also be raised as to the inocuousness of the recommended ion exchange resins (sulfonated copolymers of styrene and of divinylbenzene in particular) in terms of protection of the environment.

In his concern to improve the anticryptogamic effectiveness of the sources of copper ions $Cu^{++}$ available to him, the technician skilled in the art has also turned towards formulations associating cupric compounds on the one hand and acupric synthetic substances on the other hand. With this objective, the latter may be contact agents such as the aforementioned derivatives of carbamic acid or of phthalimide and/or systemic agents of the alkylphosphite type.

Such formulations associating an antimildew agent with contact action, whether it be of a cupric nature or not, and an antimildew agent with systemic action of the alkylphosphite type are described in patents FR 2,377,155 and FR 2,555,411. The complementary effect over time of these two types of agents proves to be particularly beneficial in the battle against the *Plasmopara viticola*.

However, the principle drawback encountered in the use of synthetic substances resides in their toxicity with respect to the environment.

The effects of these products on the natural surroundings are difficult to evaluate and oblige the manufacturers of phytosanitary compositions to conduct studies of a toxicological or ecological character which are long and expensive.

It results from the foregoing that there existed a real need to make available to the public a phytosanitary composition using the properties of copper ions $Cu^{++}$, capable of being employed at a quantitative level distinctly lower than traditional cupric formulations and showing no secondary effect with a toxicological or ecological character.

It is hence an object of the invention to overcome the drawbacks of the prior art and to provide a cupric phytosanitary composition responding better than those already existing to the various exigencies of practice.

And the Applicants have had the merit of finding that this object could be atteined when phytosanitary compositions of the type concerned include at least one cyclodextrin adapted to form complexes with the copper ions $Cu^{++}$.

Applicants have particularly observed that, surprisingly and unexpectedly, the phytosanitary compositions according to the invention had among others as an advantage that of being effective at doses calculated in copper equivalent distinctly lower than those required in the use of traditional cupric products.

Without wishing to be bound by any particular theory, it seems that the high effectiveness of the compositions according to the invention is due to the fact that not only the complexes adapted to be formed between cyclodextrins and copper ions $Cu^{++}$ contained in and/or released from the copper source are capable of being dissociated under the effect of rain and of surrounding moisture and hence of making available said active $Cu^{++}$ ions, but also this dissociation occurs progressively avoiding any superfluous release and any washing of this active substance.

Consequently, the phytosanitary compositions according to the invention, useful especially in the protection of plants against cryptogamic diseases, is characterized by the fact that it contains a source of $Cu^{++}$ ions and at least one cyclodextrin adapted to form complexes with said copper ions.

By a source of $Cu^{++}$ ions, is meant any composition containing and/or capable of releasing, directly or not, said ions.

Preferably, said source of copper ions comprises at least one inorganic copper salt, particularly selected from the group comprising copper sulphate, copper hydroxide, copper oxychloride and cuprous oxide.

Still more preferably, said source of copper ions is constituted principally of copper sulphate and/or copper hydroxide.

As copper sources which can advantageously be employed within the scope of the invention, may be mentioned the compositions of the "Bordeaux mixture" or "Burgundian mixture" previously mentioned and useful, for example, for the protection of vine against *Plasmopara viticola*.

By the term "cyclodextrin", is meant any macrocycle constructed from six, seven or eight glucose units and denoted respectively by alpha, beta or gamma cyclodextrine, as well as any derivative of any one of the latter. The term "derivative" must be understood as comprising any macrocycle such as has just been defined one at least of its constituent glucose units being substituted, at least at one spot, by a group or a molecule which can be of very divers size and functionality, as for example, an alkyl group and particularly an hydroxyalkyl group such as a hydroxypropyl group or a molecule of mono- or disaccharide such as a molecule of maltose, glucose, fructose or saccharose.

Preferably, there is employed, within the scope of the invention, at least one cyclodextrin selected from the group comprising $\beta$-cyclodextrin and etherified derivatives of the latter, especially hydroxyalkylated derivatives.

The employment of $\beta$-cyclodextrin (denoted below by BCD) and/or hydroxypropylated $\beta$-cyclodextrin (denoted below by HPBCD) appears as particularly advantageous.

The non-toxicity and the biodegradability of the cyclodextrins render the phytosanitary compositions according to the invention perfectly tolerated by the natural surroundings.

Generally, there will be used in said compositions a ratio by weight between cyclodextrin(s) and $Cu^{++}$ copper ions comprised between 0.1/1 and 10/1, preferably comprised between 0.2/1 and 5/1 and still more preferably comprised between 0.25/1 and 2.5/1.

These compositions could be in very varied solid or liquid forms and, for example, in the form of wettable powders, of concentrated suspensions, of slurries, aerosols, dusting or dispersion powders, solutions, water-soluble concentrates, emulsifiable concentrates, emulsions, etc.

It would be possible to ressort, in particular, to liquid forms and especially to slurries, dispersions, solutions, emulsions, containing from 50 to 500 g, preferably from 100 to 300 g of copper ions per hectoliter of composition. Said liquid forms will, for example, be applicable by spraying, in particular by spraying on the leaves and/or fruits of the plants to be treated.

As regards the formulation of the phytosanitary compositions according to the invention, for example, in the form of wettable powders or powders to be sprayed, the characteristic presence of cyclodextrin(s) within these compositions, does not prevent the latter from being supplemented in any way with aiding substances habitually used in this application thus as, in particular, wetting agents and dispersing agents as well as, if necessary, stabilizing agents and/or other additives like penetration agents, adhesives or anticlumping agents, coloring substances, etc.

Applicants have also been able to observe that not only the presence of cyclodextrin(s) does not prevent in any way these adjuvents from playing the role which is allocated to them, but that moreover the compositions according to the invention generally had an adhesive and covering power which is improved with respect to that of traditional cupric compositions, for example of the Bordeaux mixture type, this power coming, to a certain extent, to further reinforce and prolong the anticryptogamic action, especially fungicidal, of copper $Cu^{++}$ ions.

On the other hand, the presence of cyclodextrin(s) within the phytosanitary compositions according to the invention does not prevent in any way the latter from being able to conjointly contain one or several other active substances, especially fungicides, and in particular one or several "copperless" synthetic organic substances, such as the contact agents or systemic agents previously mentioned.

As regards the method of preparation of the compositions according to the invention, the latter remains simple and does not necessitate in any way the availability of devices and other technical means, expensive and/or delicate to employ. It is desirable however for this preparation to be carried out under conditions best ensuring the obtaining of an intimate mixture between cyclodextrin(s) and copper ion source and conferring thereby on said mixture a good aptitude to the formation of complexes between cyclodextrins and copper $Cu^{++}$ ions.

As has been seen previously, the remarkable effectiveness of the compositions according to the invention may be explained by the fact that said complexes are progressively dissociated under the action of rain and of environmental moisture, Applicants having furthermore found that the principle parameter influencing this dissociation was the pH encountered in the natural surroundings, the latter being found as substantially different from the optimal pH range required for ensuring the formation of said complexes Consequently, the preparation of the phytosanitary compositions according to the invention will be preferably carried out within the pH range ensuring, even for short mixing times, good complexation between cyclodextrin(s) and $Cu^{++}$ copper ions.

In this respect, Applicants have established, by complexometric determinations which will be presented subsequently, the fact that the ability of cyclodextrins to form complexes with copper was optimal in alkaline media, media whose pH is situated between about 10 and 13 and especially of the order of about 11 to 12, being revealed as particularly propicious for the use of $\beta$-cyclodextrin (BCD) or of derivatives of the latter, for example of the hydroxypropylated type (HPBCD).

In any event, the adjustment of the pH of the medium, if required, can be done by means of any usual alkaline agent and especially by means of sodium, potassium hydroxide, sodium carbonate or lime.

The compositions according to the invention may advantageously be prepared by malaxation of the one or more cyclodextrin(s) and the copper ion source in the presence of water and of the alkaline agent possibly necessary. The amount of water contained within these compositions does not constitute a particularly important parameter within the scope of the present invention. However, care is to be taken that the amount of water introduced be sufficiently large to avoid the use of powerful mechanical means which would be required due to the fact of the high viscosity levels reached. On the other hand, an excess of water which would result in excessive cost of separation and drying, is to be avoided.

In practice, the amount of water introduced into the malaxator represents from 30 to 60% by weight of the $Cu^{++}$ copper ion source/cyclodextrin(s) mixture employed.

Care will also be taken, in the course of the malaxating operation, to limit the heating of the preparation so as to avoid formation of black oxide. To this end, it will be preferred, in practice, to keep the temperature below 50° C.

The malaxation time must be sufficient to ensure the production of a homogeneous medium, and, in particular, to ensure a contact time between copper source and cyclodextrin(s) sufficient to facilitate the complexation of the copper $Cu^{++}$ ions. In practice, a duration of malaxation of the order of 1 h. to 2 h. enables this objective to be atteined. This duration will of course be influenced by the effectiveness of the mixing system.

After malaxation, the compositions obtained can be dried then ground and this, by any conventional means, so as to be usable in the form of wettable powders.

As has been specified, these compositions may be supplemented by means of substances customarily used in this application and in particular ionic or non-ionic wetting agents, which ensure homogeneity of the product during its employment and by further improving the distribution on plants during spray.

By way of indication, wetting agents such as esters of diethyleneglycol, oxyethylenated alkylphenols and derivatives, condensates of ethylene oxide and terpene, ethylene oxide polymers, terpene alcohols, fatty amines, etc. may validly be used in phytosanitary compositions according to the invention, especially those presented in the form of wettable powders.

In any event, whatever be the form of presentation and/or of adjuvantation of the phytosanitary compositions according to the invention, there are provided novel industrial products having undeniable advantages with respect to traditional phytosanitary compositions using copper $Cu^{++}$ ions as active substance. The compositions according to the invention enable both underdosing in copper and/or spacing of the curative and/or preventive phytosanitary treatments and this, without the effectiveness of said treatments being disturbed. The phytotoxicity of the copper sources is found to be reduced, the drawbacks associated with the use of large doses of copper are thus reduced.

From another aspect, the cyclodextrins are derived from renewable vegetable materials, namely from starchy materials, and their biodegradability and their non-toxicity render these substances perfectly tolerated by the environment.

Thus, the compositions according to the invention, whose use appears very certain from the ecological point of view, have considerable advantages through their distinctly improved effectiveness with respect to the cupric compositions of the prior art and through their absence of side effects troublesome for the environment, in particular in comparison with synthetic phytosanitary substances.

If the use of said compositions is necessary particularly for the protection of the vine against *Plasmopara viticola*, it is clear that the latter can, generally, be advantageously employed to combate, within the scope of preventive and/or curative treatements against many phytopathogenic cryptogams, especially of bacterial or fungal origin and in particular against fungi belonging to the order of Peronosporales.

In fact, the compositions according to the invention will find there usefulness in any phytosanitary treatment justifying the employment, as active substance, of copper $Cu^{++}$ ions and this, independently of the incriminated phytopathogenic agent, of the plant to be treated (vine but also fruit crops such as apple trees, pear trees, strawberry plants, vegetable crops such as lettuce, tomatoes, peas, cabbages, cereal crops, etc.) and of the elements which have to be treated, whether they are especially plants and/or parts of plants, including seeds, which can be contaminated or which are already contaminated, but also, for example, elements, and particularly soils and growth substrates, containers and cultivation, harvesting, storage and transport equipment, already in contact or intended to be placed in contact with these plants or plant parts.

The invention will be still better understandable by means of the examples which follow and which describe certain particularly advantageous embodiments of compositions according to the invention.

EXAMPLE 1

In this example, the complexing power of β-cyclodextrin with respect to copper according to the procedure described below is studied. In distilled water there is prepared a solution with 4 g/l of β-cyclodextrin, the β-cyclodextrin used being that marketed by Applicants under the mark KLEPTOSE ®. In 50 ml of solution so obtained, is added 2 ml of a 2% solution of potassium ferrocyanide ($K_4 Fe(CN)_6, 3H_2O$). The pH of the medium is adjusted to the desired value by means of sodium hydroxide or of hydrochloric acid.

In this preparation is measured a 0.1M copper sulphate solution until the appearance of a persistent brown precipitate, care being taken to maintain the pH at the desired value by means of sodium hydroxide.

The results expressed in mg of copper complexed per g of β-cyclodextrin (BCD) are collected in table I below.

TABLE I

| pH | Copper complexed in mg per g of BCD |
|---|---|
| 5 | 95 |
| 7 | 102 |
| 9 | 102 |
| 10 | 235 |
| 11 | 1245 |
| 12 | 940 |
| 13 | 210 |

It appears from table I that the complexing power of β-cyclodextrin with respect to copper is manifested preferentially within the pH range comprised between about 10 and 13 and particularly between about pH 11 and 12.

EXAMPLE 2

In this example, the procedure as described in example 1 is repeated, excepted that the β-cyclodextrin (BCD) is replaced by a hydroxypropylated derivative of the latter, also manufactured by Applicants. In the present case, the hydroxypropyl β-cyclodextrin employed has a degree of substitution (DS) of about 0.5, being understood that the concept of DS has to be attached to the average number of substituent groups, in the present case hydroxypropylated groups, borne per constituent glucose unit of the macrocycle.

The results, expressed in mg of copper complexed per g of hydroxypropyl β-cyclodextrin (HPBCD) are collected in table II below.

TABLE II

| pH | Copper complexed in mg per g of HPBCD |
|---|---|
| 5 | 45 |
| 7 | 45 |
| 9 | 51 |
| 10 | 70 |
| 11 | 245 |
| 12 | 200 |
| 13 | 25 |

The results of table II show that the complexing power of HPBCD with respect to copper, while is overall less than that of the unsubstituted product (BCD), is also optimum for the pH-range situated between about 10 and 13 and especially between about 11 and 12.

EXAMPLE 3

A wettable powder is prepared from a composition of the "Bordeaux mixture" type, that is to say whose source of copper $Cu^{++}$ ions is constituted by copper sulphate, which is placed in the presence of lime. According to the invention, there is employed, within the composition, a cyclodextrin adapted to form complexes with the copper $Cu^{++}$ ions, in the event β-cyclodextrin (BCD) marketed by Applicants under the trademark KLEPTOSE ®.

Into a malaxator are introduced the following in the order indicated:

| | |
|---|---|
| Drinking water | 1 900 g |
| BCD KLEPTOSE ® | 300 g |
| NaOH | 21 g |
| Copper sulphate | 1 200 g |
| Lime | 400 g. |

The suspension is mixed for two hours. The temperature is controlled by means of a cooling system in order to keep it below 50° C.

At the end of the operation, the pH of the composition is equal to 11.2, that is to say within the domain of pH where the degree of complexation of the copper by the β-cyclodextrin is observed to be highest according to table I above.

The preparation is then dried and then ground to a particle size less than 70 μm.

EXAMPLE 4

In this example, the same composition as in example 3 is prepared, except that NaOH is no longer employed. After two hours mixing, the pH of the preparation is equal to 9.9. The composition is then dried and ground in the same manner as for example 3.

EXAMPLE 5

In this example, the procedure of preparation described for example 3, is respected, apart from the ratio of β-cyclodextrin (BCD) with respect to the copper is increased:

| | |
|---|---|
| Drinking water | 2 040 g |
| BCD KLEPTOSE ® | 450 g |
| NaOH | 20 g |
| Copper sulphate | 1 200 g |
| Lime | 400 g. |

After mixing, the pH of the composition is equal to 11.1. The preparation is then dried, then ground so as to be presented in the form of a wettable powder.

EXAMPLE 6

The preparation described here is identical with that of example 5, except that the introduction of NaOH is eliminated. The pH of the preparation after malaxation is equal to 10.2.

EXAMPLE 7

In this example, the same protocole of preparation as that used for examples 3 and 5 is respected, the ratio of β-cyclodextrin (BCD) with respect to the copper being however increased:

| | |
|---|---|
| Drinking water | 2 200 g |
| BCD KLEPTOSE ® | 600 g |
| NaOH | 22 g |
| Copper sulphate | 1 200 g |
| Lime | 400 g |

After two hours of mixing, the pH of the composition is equal to 11.0. The preparation is then dried and ground to the state of wettable powder.

EXAMPLE 8

In this example, the association copper sulphate/lime is replaced by a source of copper constituted solely by copper hydroxide ($Cu(OH)_2$).

Into a malaxator are introduced the following substances in the order indicated:

| | |
|---|---|
| Drinking water | 1 060 g |
| BCD KLEPTOSE ® | 600 g |
| Copper hydroxide | 460 g |
| NaOH | 1.1 g |

The suspension is mixed for 2 hours during which the temperature is kept below 50° C. by means of a cooling system.

After the mixing, the pH of the composition is equal to 11.1.

The composition is dried and ground to a particle size less than 70 μm to be presented in the form of a wettable powder.

EXAMPLE 9

Groups of 8 plots of 4 young vine plants (Cabernet-Sauvignon) are treated from 22 Jul., the treatments then being spaced by 14 days, with slurries obtained from one or the other of the following compositions:

Composition A =
composition according to the invention described in example 3;

Composition B =
composition according to the invention described in example 4;

Composition C =
composition according to the invention described in example 5;

Composition D =
composition according to the invention described in example 6;

Composition E =
composition according to the invention described in example 7;

Composition F =
composition according to the invention described in example 8.

The slurries prepared by means of these compositions are supplemented with the wetting agent marketed by DU PONT DE NEMOURS under the name "spreader sticker" in portion of 80 ml per hectoliter.

These treatments are carried out in the proportion of 1000 l/ha.

On Aug. 2, an artificial contamination of vine plants is performed with a strain of *Plasmopara viticola*.

On the 17th and 26th of Aug., a panel of judges carries out a check of the young plants treated by visual and overall evaluation with respect to untreated control plants. The marking takes into account the general state of the plant, the essential factor being the percentage of foliage affected with mildew.

As controls, there was also treated, and this, according to the usage doses recommended by the manufacturer, two groups of 8 plots one with a conventional cupric composition marketed by R.S.R. under the name "R.S.R. Bordeaux mixture", the other with a synthetic fungicide marketed by ROHM & HAAS under the name "Dithane M 45" based on the derivative of carbamic acid known under the name of "mancozebe".

The results obtained are collected in tables III and IV below. The concentrations of the compositions are expressed in content of metallic copper for the cupric compounds and as active substance ["mancozebe" or double ethylene bis (dithiocarbamate) of zinc and manganese] for the synthetic fungicide.

TABLE III

| Composition | Dose of active substance (metallic copper or the like) in g/hl | Weight Ratio BCD/copper | % foliage affected 08/17 | % foliage affected 08/26 |
|---|---|---|---|---|
| Untreated control | — | — | 67.8 | 89.4 |
| Bordeaux mixture Control | 300 | — | 5.6 | 28.8 |
| Synthetic fungicide Control | 280 | — | 9.1 | 35.6 |
| Composition A | 300 | 1 | 4.8 | 23.4 |
| Composition E | 300 | 2 | 6.4 | 28.8 |
| Composition F | 300 | 2 | 4.5 | 13.1 |

The damages caused on the untreated control show that the attack of the mildew was particularly severe during this test.

The results obtained by employing compositions according to the invention, that is to say based on copper and cyclodextrin(s), show that the presence of cyclodextrin(s) within these compositions permits overall the effectiveness to be improved in terms of fungicidal activity.

In this respect, the combination copper/β-cyclodextrin (composition F) appears here as particularly effective.

In the present case, i.e. in the case of compositions measured out at 300 g/hl of metallic copper, the combination copper sulphate/β-cyclodextrin (composition A) appears particularly advantageous for a ratio by weight BCD/copper of the order of 1/1.

TABLE IV

| Composition | Dose of active substance (metallic copper or the like) in g/hl | Weight Ratio BCD/copper | % foliage affected 08/17 | % foliage affected 08/26 |
|---|---|---|---|---|
| Bordeaux mixture Control | 300 | — | 5.6 | 28.8 |
| Composition A | 150 | 1 | 8.6 | 25.9 |
| Composition B | 150 | 1 | 9.1 | 25.9 |
| Composition F | 150 | 2 | 11.7 | 29.1 |
| Composition C | 100 | 1.5 | 7.5 | 30.0 |
| Composition D | 100 | 1.5 | 9.8 | 34.4 |
| Synthetic fungicide Control | 280 | — | 9.1 | 35.6 |

The results of table IV show overall that the composition according to the invention permits a notable reduction of the amount of copper sprayed on the vine plants whilst ensuring thereof an effective protection against the development of *Plasmopara viticola*.

The compositions according to the invention titrating at 150 g/hl of metallic copper are revealed to be as effective as, even more effective than a conventional Bordeaux mixture, that is to say free from cyclodextrin(s), which contain however twice times more metallic copper.

The compositions according to the invention tested at 100 g/hl of metallic copper are hardly less effective than the conventional Bordeaux mixture. These products remain superior to the control synthetic fungicide and show the advantage, like those titrating at 150 g/hl of metallic copper moreover, of not revealing any sign of phytotoxicity against the vine and particularly no trace of burns.

EXAMPLE 10

Groups of 6 elementary plots of 4 fruit bearing vine stocks (Muscadet vine variety) are treated from the 6th of Jun., the treatements being spaced by 14 days, and this up to 16th of Aug., with slurries obtained from the abovesaid compositions A, C and F.

These treatments are carried out in the proportion of 1000 l/ha. Two artificial contaminations with a strain of *Plasmopara viticola*, were carried out, one on Jun. 14 on the leaves and the other on Jun. 26 on the clusters.

On Jul. 20 and Aug. 9, a panel of judges carried out a check of treated and untreated vine stocks by visual evaluation of the general condition of the grape production after the attack of the mildew.

The marking takes into account the percentage of clusters attacked, even partially, by the mildew.

On the other hand, in the observation of Aug. 9, said panel estimated the percentage by weight of grapes which had undergone a significant damage, this estimate being in fact the essential parameter taken into account by the farmer.

As a control, two groups of six plots were also treated, one with the cupric composition called "R.S.R. Bordeaux mixture", the other with the synthetic fungicide "Dithane M 45".

The results obtained are collected in table V below. The compositions are expressed in content of metallic copper for the cupric compounds and in active substance ("mancozebe") for the synthetic fungicide.

TABLE V

| Composition | Dose of active substance (g/hl) | Weight Ratio BCD/Cu | % attack on grapes 07/20 | % attack on grapes 08/09 | % damages 08/09 |
|---|---|---|---|---|---|
| Untreated control | — | — | 54.8 | 99 | 54.8 |
| Bordeaux mixture Control | 300 | — | 16.8 | 75.9 | 16.8 |
| Synthetic fungicide Control | 280 | — | 11.9 | 57 | 11.9 |
| Composition A | 150 | 1 | 9.5 | 62.3 | 9.5 |
| Composition C | 100 | 1.5 | 15.4 | 71.7 | 15.4 |
| Composition F | 150 | 2 | 10.7 | 61.3 | 10.7 |

The results of table V show that the compositions according to the invention enable a notable reduction in the amount of copper sprayed onto the vine stocks in production whilst ensuring effective protection thereof against the development of mildew.

The compositions titrating 150 g/hl of copper are shown to be as effective as, even more effective than the conventional Bordeaux mixture which is used at 300 g/hl of copper, i.e. double in active substance.

The composition according to the invention tested at 100 g/hl of metallic copper is as effective as the conventional Bordeaux mixture.

It has been possible to make similar observations as regards the attack of the foliage and this until the fall of the leaves.

The compositions according to the invention have the advantage of not showing any sign of phytotoxicity and in particular no trace of burn.

EXAMPLE 11

By way of comparison, there were tested according to the same procedure as previously, plots of vine plants with the aid of compositions prepared by the employment in water, just before use, on the one hand of a conventional cupric product (R.S.R. Bordeaux mixture) in powder form and, on the other hand, of β-cyclodextrin (BCD) KLEPTOSE® in powder form.

The results obtained are collected in table VI below:

TABLE VI

| Dose of Bordeaux mixture in g/hl | Dose of copper in g/hl | Dose of BCD KLEPTOSE in g/hl | Weight Ratio BCD/Cu | % foliage affected 08/17 | % foliage affected 08/26 |
|---|---|---|---|---|---|
| 1500 | 300 | 0 (control) | — | 5.6 | 28.8 |
| 1500 | 300 | 75 | 0.25 | 6.4 | 23.1 |
| 1500 | 300 | 150 | 0.50 | 6.6 | 21.3 |
| 1500 | 300 | 300 | 1 | 9.2 | 20.3 |
| 1500 | 300 | 600 | 2 | 10.5 | 19.1 |
| 1000 | 200 | 150 | 0.75 | 6.3 | 19.7 |

It is concluded from the results of table VI that the source of copper $Cu^{++}$ ions employed in the phytosanitary compositions according to the invention can advantageously be constituted from a cupric composition already existing on the market and particularly of the "Bordeaux mixture" type.

In addition, the characteristic presence of cyclodextrin(s) in the compositions according to the invention, and particularly of β-cyclodextrin (BCD) enables the effectiveness of $Cu^{++}$ copper ions sources employed to be significantly increased and this, even for ratios by weight BCD/copper of the order of 0.25.

This surprising effectiveness can be put to profit by the preparations of anticryptogamic compositions whose content of copper and hence potential toxicity with respect to plants and the environment, is significantly reduced relative to traditional cupric products.

We claim:

1. Phytosanitary composition, useful for the protection of plants against cryptogamic diseases, essentially consisting of a source of $Cu^{++}$ copper ions and one cyclodextrin adapted to form complexes with said copper ions.

2. Composition according to claim 1, wherein the source of $Cu^{++}$ copper ions is an inorganic copper salt.

3. Composition according to claim 1, wherein the source of $Cu^{++}$ copper ions is selected from the group consisting of copper sulphate, copper hydroxide, copper oxychloride and cuprous oxide.

4. Composition according to claim 1, wherein the source of $Cu^{++}$ copper ions is selected from the group consisting of copper sulphate, copper hydroxide and their mixtures.

5. Composition according to claim 1 wherein the source of $Cu^{++}$ copper ions is of the Bordeaux mixture or Burgundian mixture type.

6. Composition according to claim 1, wherein the cyclodextrin is β-cyclodextrin or a derivative of the latter.

7. Composition according to claim 1 wherein the cyclodextrin is an alkylated β-cyclodextrin.

8. Composition according to claim 1, wherein the cyclodextrin is an hydroxyalkylated β-cyclodextrin.

9. Composition according to claim 1, wherein the cyclodextrin is an hydroxypropylated β-cyclodextrin.

10. Composition according to claim 1, wherein the cyclodextrin is a β-cyclodextrin substituted by a monosaccharide or a disaccharide.

11. Composition according to claim 1, wherein the cyclodextrin is a β-cyclodextrin substituted by a mono- or disaccharide selected from the group consisting of maltose, glucose, fructose or saccharose.

12. Composition according to claim 1, wherein the ratio by weight cyclodextrin/copper ion is selected between 0.1/1 and 10/1.

13. Composition according to claim 1, wherein the ratio by weight cyclodextrin/copper ion is selected between 0.2/1 and 5/1.

14. Composition according to claim 1, wherein the ratio by weight cyclodextrin/copper ion is selected between 0.25/1 and 2.5/1.

15. Composition according to claim 1, in a form selected from the group consisting of a wettable powder, a spray powder, a concentrated suspension, a powder for dusting, a dispersion, a solution, a water-soluble concentrate, an emulsifiable concentrate, an emulsion and an aerosol.

16. Composition according to claim 1, is a liquid form selected from the group consisting of a slurry, a solution, a dispersion or an emulsion and containing from 50 to 500 g of copper ions per hectoliter of composition.

17. Composition according to claim 1, is a liquid form selected from the group consisting of a slurry, a solution, a dispersion or an emulsion and containing from 100 to 300 g of copper ions per hectoliter of composition.

18. Process for the preparation of a phytosanitary composition, useful for the protection of plants against cryptogamic diseases, comprising mixing a source of $Cu^{++}$ copper ions with a cyclodextrin, in a ratio by weight cyclodextrin/copper ions comprised between 0.1/1 and 10/1.

19. Process for the preparation of a phytosanitary composition according to claim 18, wherein during said mixing, the pH is brought and then kept between about 10 and 13 and the temperature maintained less than about 50° C.

20. Process for the preparation of a phytosanitary composition according to claim 18, wherein:
the source of copper ions employed is selected from the group consisting of copper sulphate, copper hydroxide, and their mixtures,
the cyclodextrin employed is β-cyclodextrin,
the ratio by weight β-cyclodextrin/copper ions employed is comprised between 0.2/1 and 5/1.

21. Process for the preparation of a phytosanitary composition according to claim 18, wherein:
the source of copper ions employed is selected from the group consisting of copper sulphate, copper hydroxide, and their mixtures,
the cyclodextrin employed is β-cyclodextrin,
the ratio by weight β-cyclodextrin/copper ions employed is comprised between 0.25/1 and 2.5/1.

22. Process for the preparation of a phytosanitary mixture according to claim 18, wherein,
the source of copper ions employed is of the Bordeaux mixture or Burgundian mixture type,
the cyclodextrin employed is β-cyclodextrin,
the ratio by weight β-cyclodextrin/copper ions employed is comprised between 0.2/1 and 5/1.

23. Process for the preparation of a phytosanitary mixture according to claim 18, wherein:
the source of copper ions employed is of the Bordeaux mixture of Burgundian mixture type,
the cyclodextrin employed is β-cyclodextrin,
the ratio by weight β-cyclodextrin/copper ions employed is comprised between 0.25/1 and 2.5/1.

24. Method of phytosanitary treatment to protect plants against cryptogamic diseases, wherein there is applied a composition according to claim 1 to substrates selected from the group consisting of plants, portions of plants, seeds, soils and growth substrates, containers, culture equipment, harvesting equipment, storage equipment and transport equipment, already in contact or intended to be placed in contact with these plants or portions of plants.

25. Method of protecting a plant consisting of vine against *Plasmopara vitocola* or mildew of the vine, wherein there is applied a phytosanitary composition according to claim 1.

26. Method of protecting a plant consisting of vine against *Plasmopara vitocola* or mildew of the vine, wherein there is applied by spraying a phytosanitary composition according to claim 1.

27. Method of protecting a plant consisting of vine against *Plasmopara viticola* or mildew of the vine, wherein there is applied a phytosanitary composition according to claim 1, under a liquid form and containing from 50 to 500 g of copper ions per hectoliter of composition.

* * * * *